(12) United States Patent
Grobbee

(10) Patent No.: US 10,251,733 B2
(45) Date of Patent: Apr. 9, 2019

(54) SYSTEM AND METHOD FOR MANUFACTURING LAYERED DENTURES

(71) Applicant: Global Dental Science LLC, Scottsdale, AZ (US)

(72) Inventor: Johannes Petrus Michael Grobbee, Oosterbeek (NL)

(73) Assignee: Global Dental Science LLC, Scottsdale, AZ (US)

( * ) Notice: Subject to any disclaimer, the term of this patent is extended or adjusted under 35 U.S.C. 154(b) by 0 days.

(21) Appl. No.: 14/195,348

(22) Filed: Mar. 3, 2014

(65) Prior Publication Data

US 2015/0245891 A1    Sep. 3, 2015

(51) Int. Cl.
*A61C 13/00* (2006.01)
*A61C 13/09* (2006.01)
*A61C 13/10* (2006.01)

(52) U.S. Cl.
CPC .......... *A61C 13/09* (2013.01); *A61C 13/1003* (2013.01)

(58) Field of Classification Search
CPC . A61C 13/00; A61C 13/0001; A61C 13/0024; A61C 13/0025; A61C 13/0027; A61C 13/01; A61C 13/08; A61C 13/081; A61C 13/087; A61C 13/083; A61C 13/09; A61C 13/10; A61C 13/1003; A61C 13/26; A61C 13/34
USPC .............................. 433/191, 171, 212.1, 195
See application file for complete search history.

(56) References Cited

U.S. PATENT DOCUMENTS

| | | | |
|---|---|---|---|
| 200,445 | A | 2/1878 | Fahnestock |
| 321,847 | A | 7/1885 | Peirce et al. |
| 711,324 | A | 10/1902 | Lacy |
| 830,887 | A | 9/1906 | Robert |
| 1,223,450 | A | 4/1917 | Van Allen |
| 1,293,627 | A | 2/1919 | Bowers |
| 1,585,348 | A | 5/1926 | Hick et al. |
| 1,652,910 | A | 12/1927 | Psayla |
| 1,714,185 | A | 5/1929 | Hugh |
| 1,863,591 | A | 6/1932 | Crowell |
| 1,914,606 | A | 6/1933 | Kinna et al. |
| 2,107,181 | A | 2/1938 | Guyton |
| 2,398,671 | A | 4/1947 | Harris et al. |
| 2,418,833 | A | 4/1947 | Harris et al. |

(Continued)

FOREIGN PATENT DOCUMENTS

| | | |
|---|---|---|
| CA | 2505892 | 5/2004 |
| CN | 1750797 | 3/2006 |

(Continued)

OTHER PUBLICATIONS

USPTO; Office Action dated Sep. 24, 2013 in U.S. Appl. No. 13/249,210.

(Continued)

*Primary Examiner* — Yogesh P Patel
(74) *Attorney, Agent, or Firm* — Derrick Harvey; Harvey Law

(57) ABSTRACT

A method of manufacturing a layered denture in which the enamel layer or the tooth layer is manufactured first and the denture base is manufactured last. The resulting denture may exhibit an enamel layer or a tooth layer with enhanced strength and/or resiliency. The resulting denture may have one or more of an integrated layer, balanced occlusion, and a root approximating structure.

15 Claims, 20 Drawing Sheets

(56) References Cited

U.S. PATENT DOCUMENTS

| | | |
|---|---|---|
| 2,472,492 A | 6/1949 | Saffir |
| 2,602,997 A | 7/1952 | Clawson |
| 2,641,835 A | 6/1953 | Greenmun |
| 2,985,961 A | 5/1961 | Schwartz |
| 2,994,957 A | 8/1961 | McLeod |
| 3,083,459 A | 4/1963 | McMurry et al. |
| 3,241,238 A | 3/1966 | Kertsten |
| 3,335,495 A | 8/1967 | Theodore |
| 3,458,936 A | 8/1969 | Tuccillo et al. |
| 3,470,614 A | 10/1969 | Kelly |
| 3,518,761 A | 7/1970 | Susman et al. |
| 3,644,996 A | 2/1972 | Weinkle |
| 3,667,123 A | 6/1972 | Huey |
| 3,702,027 A | 11/1972 | Marshall et al. |
| 3,727,309 A | 4/1973 | Huey |
| 3,748,739 A | 7/1973 | Thibert |
| 3,813,777 A | 6/1974 | Van Handel et al. |
| 3,839,796 A | 10/1974 | Hazar |
| 3,844,702 A | 10/1974 | Dimmer et al. |
| 3,846,911 A | 11/1974 | Wichner |
| 3,908,272 A | 9/1975 | Arnold |
| 3,937,773 A | 2/1976 | Huffman |
| 4,029,632 A | 6/1977 | Gross et al. |
| 4,227,877 A | 10/1980 | Tureaud et al. |
| 4,247,287 A | 2/1981 | Gigante |
| 4,299,573 A | 11/1981 | Ricci |
| 4,398,884 A | 8/1983 | Huffman |
| 4,533,325 A | 8/1985 | Blair |
| 4,575,340 A | 3/1986 | Lustig |
| 4,591,341 A | 5/1986 | Andrews |
| 4,634,377 A | 1/1987 | Behrend |
| 4,784,608 A | 11/1988 | Mays |
| 4,931,016 A | 6/1990 | Sillard |
| 5,030,102 A | 7/1991 | Lang |
| 5,098,296 A | 3/1992 | Cullen |
| 5,151,044 A | 9/1992 | Rotsaert |
| 5,169,309 A | 12/1992 | Staubli et al. |
| 5,188,529 A | 2/1993 | Luth |
| 5,234,339 A | 8/1993 | Grigereit |
| 5,427,906 A | 6/1995 | Hansen |
| 5,672,305 A | 7/1997 | Kogure |
| 5,711,668 A | 1/1998 | Huestis |
| 5,716,214 A | 2/1998 | Lund |
| 5,718,584 A | 2/1998 | Wong |
| 5,775,899 A | 7/1998 | Huffman |
| 5,814,575 A | 9/1998 | Reagen et al. |
| 5,833,461 A | 11/1998 | Wong |
| 5,839,900 A | 11/1998 | Billet et al. |
| 5,885,078 A | 3/1999 | Cagna et al. |
| 5,934,906 A | 8/1999 | Phimmasone |
| 5,985,170 A | 11/1999 | Inaba et al. |
| 6,030,218 A | 2/2000 | Robinson |
| 6,056,547 A | 5/2000 | Names |
| 6,116,070 A | 9/2000 | Oshida |
| 6,126,445 A | 10/2000 | Willoughby |
| 6,139,322 A | 10/2000 | Liu |
| 6,149,427 A | 11/2000 | Van Handel |
| 6,224,372 B1 | 5/2001 | Ibsen et al. |
| 6,227,851 B1 | 5/2001 | Chishti |
| 6,257,895 B1 | 7/2001 | Oestreich |
| 6,384,107 B2 | 5/2002 | Liu |
| 6,422,864 B1 | 7/2002 | Glatt |
| 6,488,503 B1 | 12/2002 | Lichkus |
| 6,616,444 B2 | 9/2003 | Andreiko et al. |
| 6,788,986 B1 | 9/2004 | Traber et al. |
| 6,851,949 B1 | 2/2005 | Sachdeva |
| 7,021,934 B2 | 4/2006 | Aravena |
| 7,153,135 B1 | 12/2006 | Thomas |
| 7,234,940 B2 | 6/2007 | Weissman |
| 7,433,810 B2 | 10/2008 | Pavloskaia et al. |
| 7,474,932 B2 | 1/2009 | Geng |
| 7,530,810 B2 | 5/2009 | Clement |
| 7,653,455 B2 | 1/2010 | Cinader, Jr. |
| 7,704,076 B2 | 4/2010 | Mullaly |
| 7,758,345 B1 | 7/2010 | Christensen |
| 7,758,346 B1 | 7/2010 | Letcher |
| 7,806,691 B2 | 10/2010 | Berger |
| 7,854,611 B2 | 12/2010 | Yau et al. |
| 7,901,209 B2 | 3/2011 | Saliger et al. |
| 7,909,607 B2 | 3/2011 | Yau et al. |
| 7,950,924 B2 | 5/2011 | Brajnovic |
| 8,043,091 B2 | 10/2011 | Schmitt |
| 8,348,669 B1 | 1/2013 | Schmitt |
| 8,567,408 B2 | 10/2013 | Roettger |
| 8,641,938 B2 | 2/2014 | Howe |
| 8,801,431 B2 | 8/2014 | Thompson et al. |
| 8,875,398 B2 | 11/2014 | Balshi et al. |
| 9,055,993 B2 | 6/2015 | Grobbee et al. |
| 9,155,599 B2 | 10/2015 | Thompson et al. |
| 9,213,784 B2 | 12/2015 | Thompson et al. |
| 9,364,302 B2 | 6/2016 | Thompson et al. |
| 9,402,698 B2 | 8/2016 | Thompson et al. |
| 9,717,572 B2 | 8/2017 | Thompson et al. |
| 9,744,010 B2 | 8/2017 | Thompson et al. |
| 2002/0015934 A1 | 2/2002 | Rubbert et al. |
| 2002/0180760 A1 | 12/2002 | Rubbert et al. |
| 2003/0108845 A1 | 6/2003 | Giovannone |
| 2003/0138756 A1 | 7/2003 | Monkmeyer |
| 2003/0162147 A1 | 8/2003 | Dequeker |
| 2003/0163291 A1 | 8/2003 | Jordan et al. |
| 2003/0211444 A1 | 11/2003 | Andrews |
| 2004/0005530 A1 | 1/2004 | Mullaly |
| 2004/0029068 A1 | 2/2004 | Sachdeva et al. |
| 2004/0185422 A1 | 9/2004 | Orth et al. |
| 2004/0219490 A1 | 11/2004 | Gartner et al. |
| 2005/0175957 A1 | 8/2005 | Haje et al. |
| 2005/0186539 A1 | 8/2005 | McLean |
| 2005/0284489 A1 | 12/2005 | Ambis |
| 2006/0040232 A1 | 2/2006 | Shoup |
| 2006/0040236 A1 | 2/2006 | Schmitt |
| 2006/0063135 A1 | 3/2006 | Mehl |
| 2006/0210945 A1 | 9/2006 | Savic et al. |
| 2006/0286507 A1 | 12/2006 | Dequeker |
| 2007/0154868 A1 | 6/2007 | Scharlack et al. |
| 2007/0190492 A1 | 8/2007 | Schmitt |
| 2007/0231774 A1 | 10/2007 | Massad |
| 2008/0085489 A1 | 4/2008 | Schmitt |
| 2008/0090207 A1 | 4/2008 | Rubbert |
| 2008/0127698 A1 | 6/2008 | Luckey et al. |
| 2008/0206710 A1 | 8/2008 | Kruth et al. |
| 2008/0206714 A1 | 8/2008 | Schmitt |
| 2008/0209974 A1 | 9/2008 | Ewolski et al. |
| 2008/0228303 A1 | 9/2008 | Schmitt |
| 2008/0300716 A1 | 12/2008 | Kopelman |
| 2009/0081618 A1 | 3/2009 | Lamar |
| 2009/0143609 A1 | 6/2009 | Araya |
| 2009/0148813 A1 | 6/2009 | Sun et al. |
| 2009/0162813 A1 | 6/2009 | Glor |
| 2009/0181346 A1 | 7/2009 | Orth |
| 2009/0287332 A1 | 11/2009 | Adusumilli et al. |
| 2009/0291407 A1 | 11/2009 | Kuo |
| 2009/0325125 A1 | 12/2009 | Diangelo et al. |
| 2010/0015572 A1 | 1/2010 | Dirkes et al. |
| 2010/0062394 A1 | 3/2010 | Jones et al. |
| 2010/0086186 A1 | 4/2010 | Zug et al. |
| 2010/0094446 A1 | 4/2010 | Balock et al. |
| 2010/0105011 A1 | 4/2010 | Karkar et al. |
| 2010/0324875 A1 | 12/2010 | Kalili |
| 2011/0045442 A1 | 2/2011 | Adusumilli |
| 2011/0112804 A1 | 5/2011 | Chishti et al. |
| 2011/0129796 A1 | 6/2011 | Riggio |
| 2011/0236856 A1 | 9/2011 | Kanazawa et al. |
| 2011/0244417 A1 | 10/2011 | Nilsen et al. |
| 2012/0058449 A1 | 3/2012 | Sklarski et al. |
| 2012/0094253 A1 | 4/2012 | Berger |
| 2012/0095732 A1 | 4/2012 | Fisker et al. |
| 2012/0100500 A1 | 4/2012 | Gao |
| 2012/0178045 A1 | 7/2012 | Massad |
| 2012/0179281 A1 | 7/2012 | Steingart et al. |
| 2012/0258426 A1* | 10/2012 | Boe .............. A61C 13/1006 433/171 |
| 2012/0285019 A1 | 11/2012 | Schechner et al. |
| 2012/0329008 A1 | 12/2012 | Fishman et al. |
| 2013/0101962 A1* | 4/2013 | Howe .............. 433/191 |

(56) References Cited

U.S. PATENT DOCUMENTS

| | | |
|---|---|---|
| 2013/0108988 A1 | 5/2013 | Simoncic |
| 2013/0209962 A1 | 8/2013 | Thompson et al. |
| 2013/0216978 A1 | 8/2013 | Thompson et al. |
| 2013/0218532 A1 | 8/2013 | Thompson et al. |
| 2013/0221554 A1 | 8/2013 | Jung et al. |
| 2013/0249132 A1 | 9/2013 | Thompson et al. |
| 2013/0280672 A1 | 10/2013 | Thompson |
| 2013/0316302 A1 | 11/2013 | Fisker |
| 2013/0337412 A1 | 12/2013 | Kwon |
| 2014/0045967 A1 | 2/2014 | Thomas et al. |
| 2014/0099600 A1 | 4/2014 | Harrison |
| 2014/0272796 A1 | 9/2014 | Grobbee et al. |
| 2015/0010885 A1 | 1/2015 | Balshi et al. |
| 2015/0037760 A1 | 2/2015 | Thompson et al. |
| 2015/0064653 A1 | 3/2015 | Grobbee et al. |
| 2015/0134094 A1 | 5/2015 | Thompson et al. |
| 2015/0230891 A1 | 8/2015 | Grobbee et al. |
| 2015/0245891 A1 | 9/2015 | Grobbee |
| 2015/0245892 A1 | 9/2015 | Grobbee |

FOREIGN PATENT DOCUMENTS

| | | |
|---|---|---|
| EP | 1062916 | 12/2000 |
| EP | 1252867 | 10/2002 |
| EP | 2915503 | 7/2016 |
| FR | 2035133 | 12/1970 |
| JP | 2008307281 | 12/2008 |
| WO | 2001032096 | 12/2001 |
| WO | WO 2003024352 | 3/2003 |
| WO | WO 2004060197 | 7/2004 |
| WO | 2009105661 | 8/2009 |
| WO | 2009105700 | 8/2009 |
| WO | WO 2009105700 | 8/2009 |
| WO | 2010022479 | 3/2010 |
| WO | WO 2012030493 | 3/2012 |
| WO | 2012041329 | 4/2012 |
| WO | 2012061652 | 5/2012 |
| WO | 2012061655 | 5/2012 |
| WO | 2012061659 | 5/2012 |
| WO | 2012061660 | 5/2012 |
| WO | 2014130536 | 8/2014 |
| WO | WO 2014159436 | 10/2014 |
| WO | 2015031062 | 3/2015 |

OTHER PUBLICATIONS

USPTO; Final Office Action dated Mar. 6, 2014 in U.S. Appl. No. 13/249,210.
USPTO; Restriction Requirement dated Dec. 23, 2013 in U.S. Appl. No. 13/823,466.
PCT; International Search Report and Written Opinion dated Jul. 18, 2012 in Application No. PCT/US2011/059230.
PCT; International Preliminary Report on Patentability dated May 8, 2013 in Application No. PCT/US2011/059230.
PCT; International Search Report and Written Opinion dated Jul. 18, 2012 in Application No. PCT/US2011/059235.
PCT; International Preliminary Report on Patentability dated May 8, 2013 in Application No. PCT/US2011/059235.
PCT; International Search Report and Written Opinion dated Jul. 9, 2012 in Application No. PCT/US2011/059239.
PCT; International Preliminary Report on Patentability dated May 8, 2013 in Application No. PCT/US2011/059239.
PCT; International Search Report and Written Opinion dated Jul. 18, 2012 in Application No. PCT/US2011/059240.
PCT; International Preliminary Report on Patentability dated May 8, 2013 in Application No. PCT/US2011/059240.
EPO; European Search Report dated Mar. 4, 2014 in Application No. 11838839.6.
USPTO; Notice of Allowance dated Jun. 6, 2014 in U.S. Appl. No. 13/249,210.
USPTO; Non-Final Office Action dated Jun. 6, 2014 in U.S. Appl. No. 13/823,466.
USPTO; Non-Final Office Action dated Jun. 20, 2014 in U.S. Appl. No. 13/830,963.
EPO; European Search Report and Opinion dated Mar. 3, 2014 in Application No. 11838843.8.
PCT; International Search Report and Written Opinion dated Jul. 25, 2014 in Application No. PCT/US2014/017136.
USPTO; Non-Final Office Action dated Oct. 23, 2014 in U.S. Appl. No. 13/823,621.
USPTO; Final Office Action dated dated Nov. 7, 2014 in U.S. Appl. No. 13/830,963.
USPTO; Office Action dated Jan. 5, 2015 in U.S. Appl. No. 12/939,136.
USPTO; Restriction Requirement dated Feb. 12, 2015 in U.S. Appl. No. 13/369,238.
USPTO; Advisory Action dated Feb. 23, 2015 in U.S. Appl. No. 13/830,963.
USPTO; Non-Final Office Action dated Dec. 19, 2014 in U.S. Appl. No. 14/013,295.
USPTO; Non-Final Office Action dated Apr. 9, 2015 in U.S. Appl. No. 12/939,138.
USPTO; Final Office Action dated Mar. 26, 2015 in U.S. Appl. No. 13/823,466.
USPTO; Notice of Allowance dated Jun. 22, 2015 in U.S. Appl. No. 13/823,621.
USPTO; Notice of Allowance dated Apr. 13, 2015 in U.S. Appl. No. 14/013,295.
European App EP11838843.8—EPO Examination Report dated Sep. 12, 2017.
European App EP14754979.4—EPO Search Report dated Sep. 7, 2016.
European App EP14774571.5—EPO Search Report dated Aug. 12, 2016.
European App EP14840991.5—EPO Search Report dated Apr. 19, 2017.
European App EP16184885.8—EPO Search Report dated Jan. 12, 2017.
PCT/US/2014/051008—International Search Report and Written Opinion dated Nov. 20, 2014.
PCT/US/2014/051008—Preliminary Report on Patentability dated Mar. 1, 2016.
Positioning handle and occlusal locks for the Teeth-in-a-Day protocol:, The Journal of Prosthetic Dentistry, 2016, Balshi et al., p. 274-278.
"A New Protocol for Immediate Functional Loading of Dental Implants", Dentistry Today, Balshi et al., Sep. 2001, vol. 20, No. 9.
U.S. Appl. No. 12/939,138—Advisory Action dated Nov. 23, 2015.
U.S. Appl. No. 12/939,1387—Notice of Allowance dated Mar. 14, 2016.
U.S. Appl. No. 12/939,141—Restriction Requirement dated Apr. 9, 2015.
U.S. Appl. No. 12/939,141—Non-Final Official Action dated Jul. 12, 2016.
U.S. Appl. No. 12/939,141—Final Official Action dated Oct. 5, 2017.
U.S. Appl. No. 13/823,621—Non-Final Official Action dated Oct. 23, 2014.
U.S. Appl. No. 13/830,963—Final Official Action dated Nov. 7, 2014.
U.S. Appl. No. 13/830,963—Final Official Action dated Feb. 23, 2016.
U.S. Appl. No. 13/830,963—Notice of Allowance dated Oct. 18, 2017.
U.S. Appl. No. 14/506,338—Non-Final Official Action dated Apr. 7, 2017.
U.S. Appl. No. 14/798,717—Restriction Requirement dated Aug. 17, 2017.
U.S. Appl. No. 14/821,097—Restriction Requirement dated Jan. 4, 2016.
U.S. Appl. No. 14/821,097—Non-Final Official Action dated Jun. 28, 2016.
U.S. Appl. No. 14/821,097—Notice of Allowance dated Apr. 20, 2017.

(56) References Cited

OTHER PUBLICATIONS

USPTO; Final Office Action dated Sep. 25, 2015 in U.S. Appl. No. 12/939,136.
USPTO; Final Office Action dated Aug. 19, 2015 in U.S. Appl. No. 12/939,138.
USPTO; Non-Final Office Action dated Sep. 21, 2015 in U.S. Appl. No. 13/369,238.
USPTO; Notice of Allowance dated Aug. 24, 2015 in U.S. Appl. No. 13/823,662.
USPTO; Non-Final Office Action dated Aug. 13, 2015 in U.S. Appl. No. 13/830,963.
USPTO; Non-Final Office Action dated Aug. 11, 2015 in U.S. Appl. No. 14/195,348.
USPTO; Restriction Requirement dated Sep. 5, 2014 in U.S. Appl. No. 13/823,621.
PCT; International Search Report and Written Opinion dated Aug. 7, 2014 in Application No. PCT/US2014/023654.

\* cited by examiner

SYSTEM AND METHOD FOR MANUFACTURING LAYERED DENTURES

FIELD OF INVENTION

The present invention relates to the field of manufacturing dentures. More particularly, the present invention relates to manufacturing of dentures having multiple material layers.

BACKGROUND OF THE INVENTION

Dentures have been manufactured for centuries to replace all or part of an individual's dentition. Dentures have been manufactured by molding the denture from casts made of the patient's edentulous or partially edentulous ridges. The manufacturing process may begin with a preliminary impression of the patient's mouth, which is usually done in silicone or alginate. This impression may be used to prepare a diagnostic cast. While making the impression, the dentist applies pressure to the soft tissues to simulate biting force and extends the borders of the mold to adjacent toothless areas to allow the dentures to better adapt to the gums. A final cast may then be formed from gypsum based on the diagnostic cast. The final cast may be filled or "waxed up" to form the denture. The denture teeth will be set in the wax. The cast with the waxed denture will be placed in a mold and injected or packed with acrylic. Once the resin has cured, the cast may be broken apart and the denture may be removed.

More recently, dentures have been manufactured by machining a void in a block of denture base material formed to match the contour of natural teeth as arranged on a maxilla or on a mandible; filling the void with a synthetic tooth material; removing a portion of the synthetic tooth material; and potentially filling the void and removing a portion of material a second time in order to create denture having teeth made of one or potentially two or more layers.

While machining has been used to form the basic shapes of dentures and denture teeth, prior innovations fail to adequately address the aesthetics and function of the denture, particularly the aesthetics at and below the gum line. For example, in a traditional denture the denture teeth mimic the appearance of a natural tooth only above the gum line because traditional denture teeth adhere to a denture baseplate rather than extending into the baseplate with roots, as would real teeth. Traditional denture teeth are made in standard shapes using injection molding or pressure molding techniques. Anatomical roots are not incorporated in these teeth because of manufacturing difficulties. Currently, a dental technician may festoon root structures in the denture base and use different coloring techniques to paint the dental base to simulate the roots. This requires additional cost, delay, and expense and does not aesthetically mimic a natural tooth as completely as an anatomical root would. Thus, there is a need for a denture having a more natural structure that will exhibit an improved aesthetic appearance.

Prior innovations also fail to adequately address the function of traditional dentures with traditional denture teeth. Dentures need to be balanced to avoid the patient's denture becoming loose or unstable during the protrusive and lateral movement of the mandible. This often requires grinding the occlusal surface of the denture teeth until the dentures remain in contact on at least three points throughout much of the movement of the mandible. Traditionally, a denture technician will set up the denture in an articulator and grind the teeth until the occlusive design of the denture is balanced. However, grinding the teeth will take away the enamel layer of the teeth, diminishing the aesthetic appearance of the teeth and functionally weakening the teeth. Thus there is a also need for a denture which is balanced, yet with unground occlusal surface (enamel) so that the denture has a more natural structure that will exhibit an improved aesthetic appearance and will not suffer from weakening of the enamel due to grinding.

Furthermore, in many dentures, for example, in those formed by machining, the base is machined first, followed by the teeth. For instance, the first layer to be formed is the denture base and the last layer to be formed is the enamel layer of the teeth. However, many manufacturing processes enhance the strength of the first layer to be formed (i.e., the denture base), for example, due to iterative molding/casting. However, in dentures, the enamel layer often experiences the greatest wear during use and needs to be the strongest layer of the denture. Thus, there is a need for a denture wherein the manufacturing process enhances the strength of the enamel layer, rather than the denture base.

SUMMARY OF THE INVENTION

In accordance with various aspects of the present invention, a method for manufacturing a layered denture is provided. A method for manufacturing a layered denture may include machining a material blank made of an enamel material wherein the machining forms a first cavity in the material blank and wherein the first cavity has a first tooth boundary and an aft cavity. The method may further include filling a first denture material in to the first cavity wherein the first denture material covers the first tooth boundary and extends into the aft cavity. Furthermore, the method may include machining the first denture material to form a second cavity in at least one of the material blank and the first denture material, filling a second denture material into the second cavity, and machining the second denture material to form a base pocket in the second denture material.

In accordance with an exemplary embodiment, a layered denture may be manufactured by iteratively adding layers to cavities or pockets in the denture under construction and then removing portions of the layers to create portions of the teeth, roots of teeth, reinforcement structures, or other features of the denture. Different layers can be formed from different materials having different strengths, colors, translucency and other material properties. Furthermore, a layered denture may be manufactured according to electronic models, such as three-dimensional digital images, wherein the design of the dentition is adjusted to achieve balanced occlusion.

In accordance with an exemplary embodiment, the material removing operations can be performed in accordance with three-dimensional digital images to create realistic dentures. The three-dimensional digital images can be created from the patient using combinations of digital scanning and bite impressions.

In accordance with an exemplary embodiment, a layered denture may be configured to approximate roots of teeth. The layered denture may have pockets configured to simulate roots when filled with a material. For example, a material may be filled in a pocket resulting in a root approximating structure so that the denture has a more realistic appearance.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

DESCRIPTION OF THE EXAMPLE EMBODIMENTS

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the appended claims.

For the sake of brevity, conventional techniques for manufacturing and construction may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical method of construction.

Figure 1:
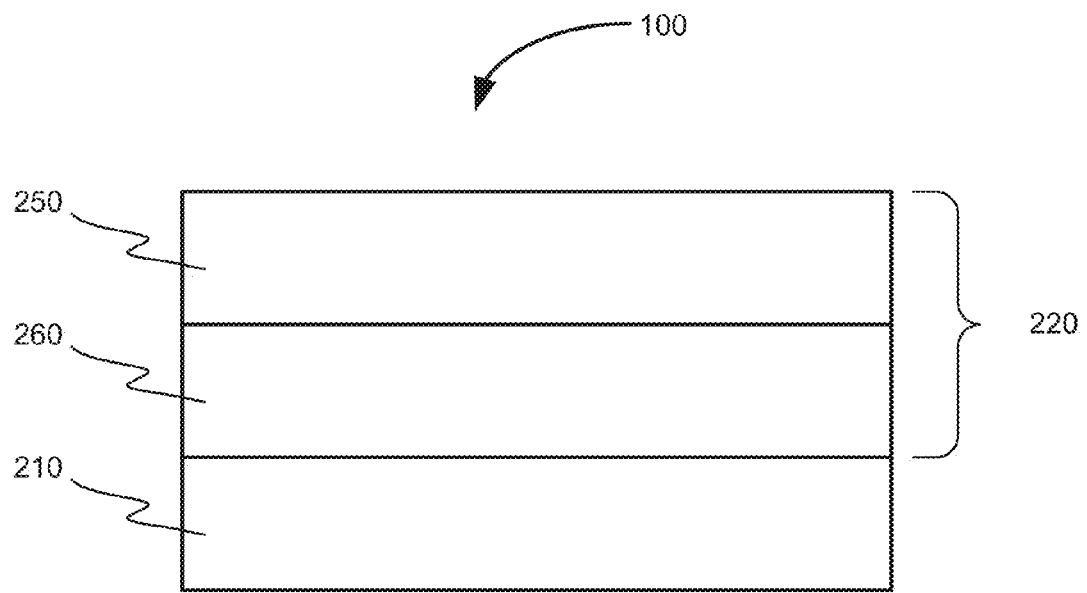
FIG. 1 is a section view of an example embodiment of a layered denture.
Figure 2:
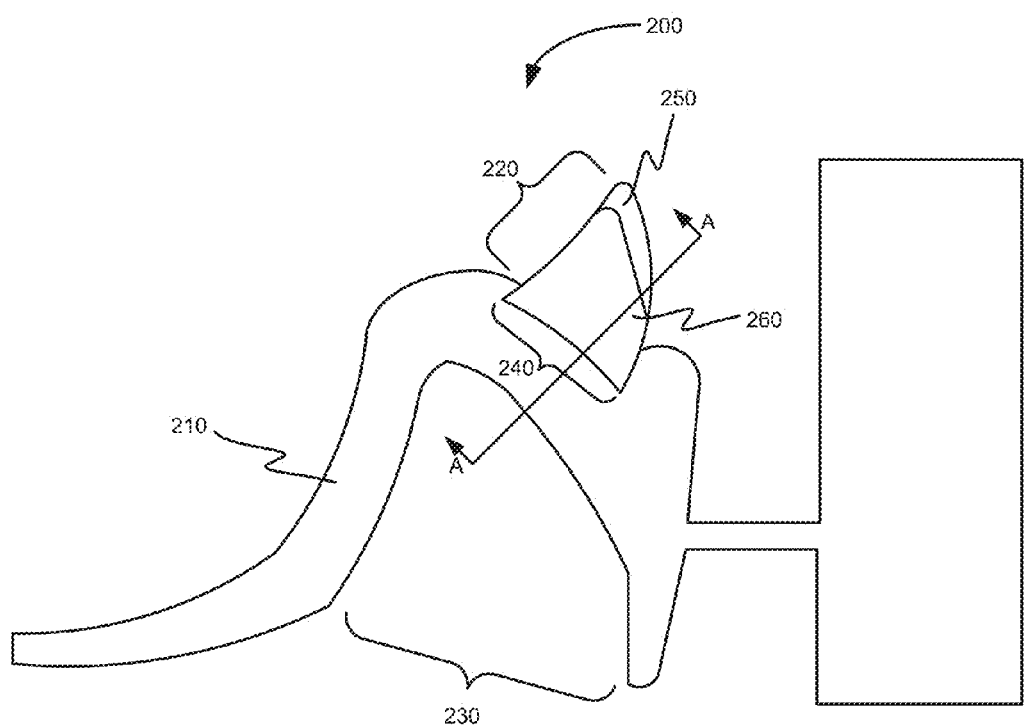
FIG. 2 is a side view of an example embodiment of a layered denture having multilayer teeth.
Figure 3:
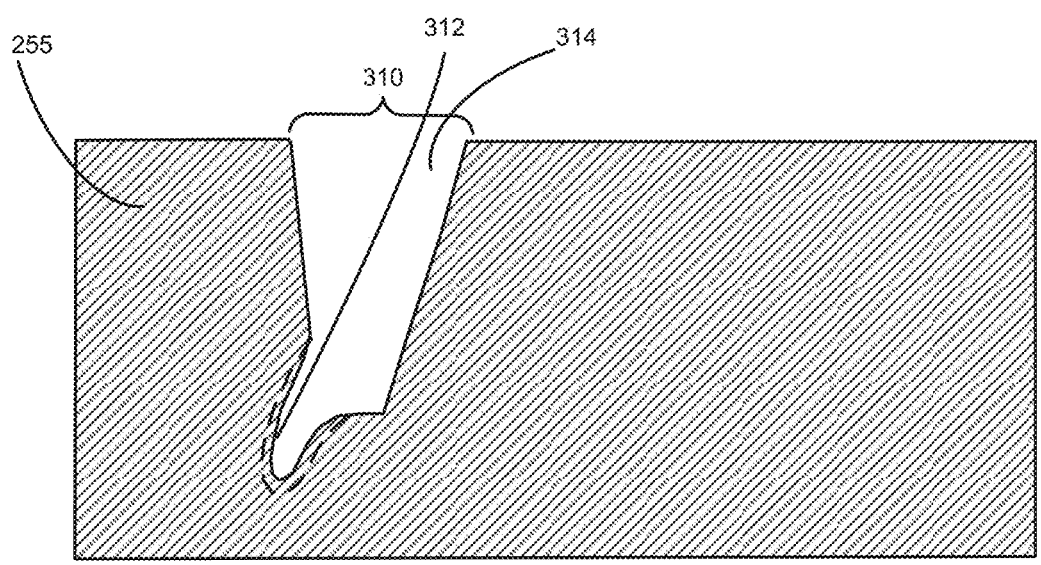
FIGS. 3-7 are side views of an exemplary layered denture having multilayer teeth at different points in an exemplary manufacturing process.
Figure 4:
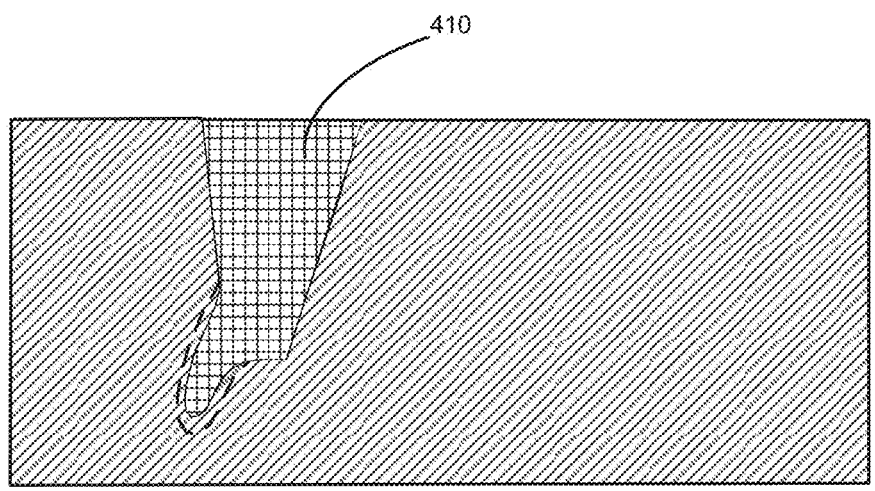
Figure 5:
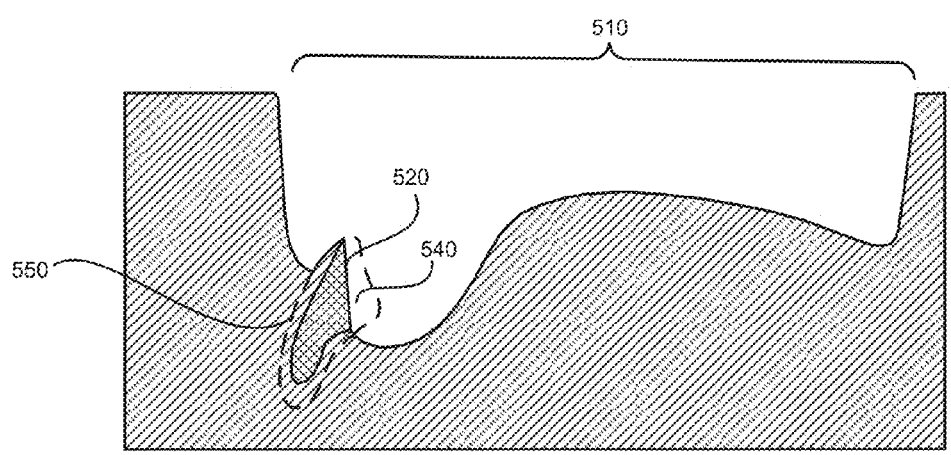
Figure 6:
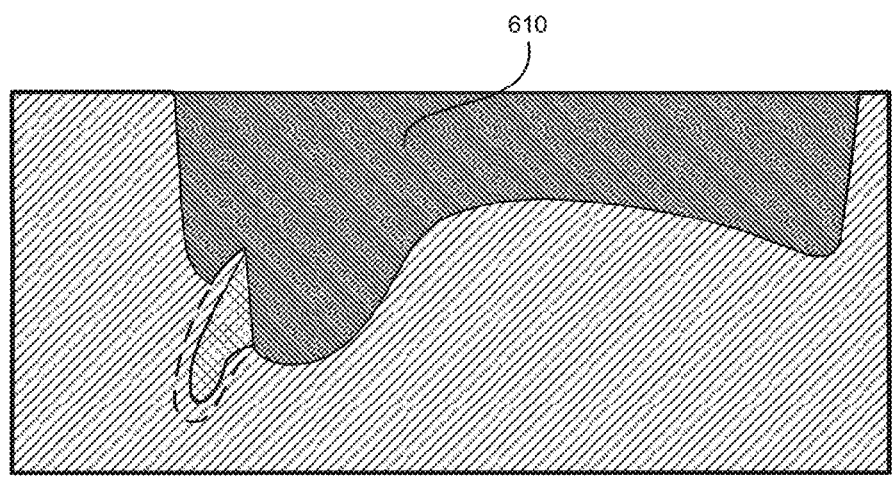
Figure 7:
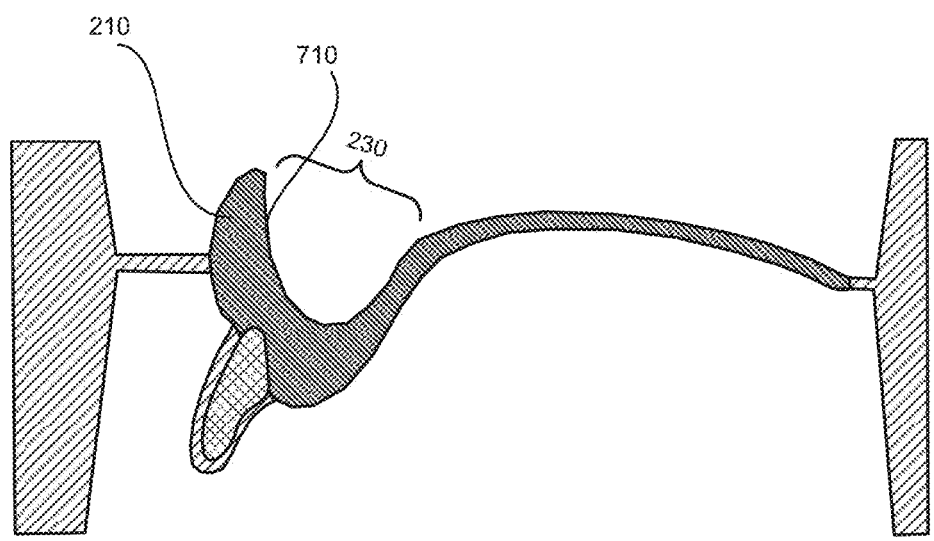

Now, with reference to FIGS. 1 and 2, a section view 100 along line A-A is provided of one example embodiment of a layered denture 200 comprising a base 210 comprising a first material having a first pocket 240; an artificial dentition structure 220 in said first pocket 240 wherein said first pocket 240 is configured to support said artificial dentition structure. An artificial dentition structure 220 may comprise a dentin layer 260 and an enamel layer 250.

In one example embodiment, said base 210 comprises a hardened polymethyl methacrylate (PMMA) material. However, said base may comprise any material having sufficiently low porosity so as to be hygienic for extended placement in a wearer's mouth. For example, said base may be made of a plastic, ceramic, metal, or acrylic, including for instance, a polymer, monomer, composite, or alloy.

Furthermore, said enamel layer 250, said dentin layer 260, said base 210 and any other components of a layered denture 200 may be formed according to a process and system for molding or forming products from thermosetting plastics. Such a system may utilize a deformable container that is placed within the cavity of a housing of a mold with resins and initiator mixed therein. As a piston slides into the cavity, the upper edges of the container may engage between the housing and the piston to seal the housing from leakage. The pressure of the piston along with heat on the housing may enable the curing process to be controlled to maximize compression and minimize porosity. Exemplary processes and systems disclosed in U.S. patent application Ser. No. 13/369,238, PROCESSES AND SYSTEMS FOR MOLDING THERMOSETTING PLASTICS are incorporated by reference.

Furthermore, said base 210 comprising a first material may have a first pocket 240. Said first pocket 240 may be machined by a CAD/CAM machining device, although any process suited for accurate forming of the material may be utilized. For example, said first pocket may be formed by machining, etching, waterjet, laser cutting, 3D printing, or chemical mask processes.

In one example embodiment, a layered denture 200 may have an artificial dentition structure 220. In one example embodiment, this structure may be at least one tooth. Said tooth may be constructed according to the principles described herein. The dentin layer 260 may comprise acrylic though any suitable material may be used. The enamel layer 250 may comprise high impact acrylic though any material adapted to be wear and abrasion resistant may be used. In some example embodiments, the dentin layer 260 and/or the enamel layer 250 comprise materials processed by exemplary processes and systems disclosed in U.S. patent application Ser. No. 13/369,238, PROCESSES AND SYSTEMS FOR MOLDING THERMOSETTING PLASTICS, which are incorporated by reference. In some example embodiments, these exemplary processes and system enhance the durability of the acrylic or other materials comprising the dentin layer 260 and/or enamel layer 250. In some example embodiments, said artificial dentition structure 220 is electronically defined to achieve balanced occlusion, in accordance with the principles disclosed herein. For example, at least one layer of said artificial dentition structure may be offset to accommodate an enamel layer.

Now, with further reference to FIG. 2, in one embodiment of a layered denture 200, base 210 is machined to conform to the geometry of a wearer's natural dentition. For example, said base 210 comprising a first material may have a base pocket 230. Said base pocket 230 may be machined by a CAD/CAM machining device, although any process suited for accurate forming of the material may be utilized. For example, said second pocket may be formed by machining, etching, waterjet, laser cutting, 3D printing, or chemical mask processes. As discussed further herein, in various embodiments, base pocket 230 may comprise an edentulous ridge interface surface 710. Moreover, in various embodiments, base pocket 230 may comprise an implant interface surface. Alternatively, base pocket 230 may comprise any configuration adapted to securely retain the layered denture in a patient's mouth.

Now, with reference to FIGS. 3-7 and FIG. 19, a layered denture may be manufactured by a process for manufacturing a layered denture 200 comprising machining a material blank 255 comprising enamel material. A first cavity 310 may be formed in the material blank 255. In various embodiments, the first cavity 310 comprises a first tooth boundary 312, and an aft cavity 314.

In various embodiments, additional material is filled into first cavity 310 and machined to form various aspects of an artificial denture. For example, a first denture material 410 may be filled into first cavity 310. The first denture material 410 may cover first tooth boundary 312 and extends into aft cavity 314. In various embodiments, the first denture material 410 comprises dentin material. In various embodiments, first denture material 410 is machined to form a second cavity 510. In various embodiments, for example, with particular reference to FIG. 5, second cavity 510 may be formed by removing portions of first denture material 410, and optionally, portions of material blank 255 comprising enamel material. In this regard, second cavity 510 may approximately outline the shape of a denture base. Moreover, a first base boundary 520 may be positioned to outline a portion of the shape of an artificial dentition structure illustrated by imaginary line 550. Moreover, the first base boundary 520 may be offset to subtract a deleted portion of an artificial dentition structure. For example, deleted portion 540 of an artificial dentition structure may be deleted via offsetting of first base boundary 520. In this manner, second cavity 510 may be shaped with consideration of aesthetic factors, such as the shaping of an artificial dentition structure illustrated by imaginary line 550, and also structural factors, such as permitting access by machining tools to the area below deleted portion 540.

In various embodiments, a second denture material is filled into second cavity 510 and machined to form various aspects of an artificial denture. The second denture material 610 may comprise denture base material. For example, a second denture material 610 comprising denture base material may be filled into second cavity 510 and machined to form a base pocket 230. In various embodiments, base pocket 230 comprises an edentulous ridge interface surface 710. In various embodiments, the edentulous ridge interface surface 710 is shaped to conform to a patient's natural mouth structures in order to securely hold the denture in a patient's mouth. Moreover, in various embodiments, base pocket 230 may comprise an implant interface surface. Alternatively, base pocket 230 may comprise any configuration adapted to securely retain the layered denture 200 in a patient's mouth.

Furthermore, in various embodiments, various other features of layered denture 200 may be further milled. For example, in various embodiments, first cavity 310 and second cavity 510 are shaped to provide slightly oversize denture features, for example, to facilitate dimensional fine-tuning via subsequent milling.

Thus, with reference to FIGS. 3-7, and FIG. 19, a novel process 1900 of manufacturing a layered denture 200 is provided. Notably, the enamel layer is formed first, followed by the dentin layer, and finally the denture base. More particularly, in various embodiments, process 1900 comprises machining a material blank comprising enamel material wherein the machining forms a first cavity, filling a first denture material into the first cavity, wherein the first denture material comprises dentin material, machining the first denture material comprising dentin material wherein the machining forms a second cavity, filling a second denture material into the second cavity wherein the second material comprises denture base material, and machining the second denture base material wherein the machining forms an edentulous ridge interface surface. In accordance with various embodiments, each material filled into a cavity may be cured prior to being milled. In various embodiments, said material is cured by exposure to heat and/or pressure. Alternatively, in various embodiments, only the material blank is cured by exposure to heat and/or pressure. In various embodiments, said material is cured by exemplary processes and systems disclosed in U.S. patent application Ser. No. 13/369,238, PROCESSES AND SYSTEMS FOR MOLDING THERMOSETTING PLASTICS, which are incorporated by reference. For instance, the curing process may enhance the strength and resiliency of the material. In this regard, it is often advantageous to form the material blank from the enamel material, thus, permitting the enamel layer to be exposed to the curing process, thus enhancing the strength of the enamel layer more so than the other layers.

Figure 8:
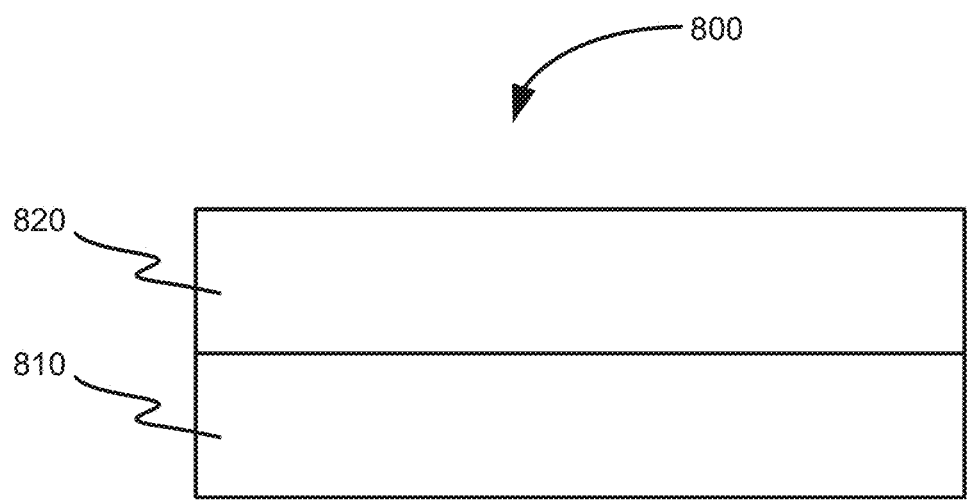
FIG. 8 is a section view of an example embodiment of a layered denture having single layer teeth.
Figure 9:
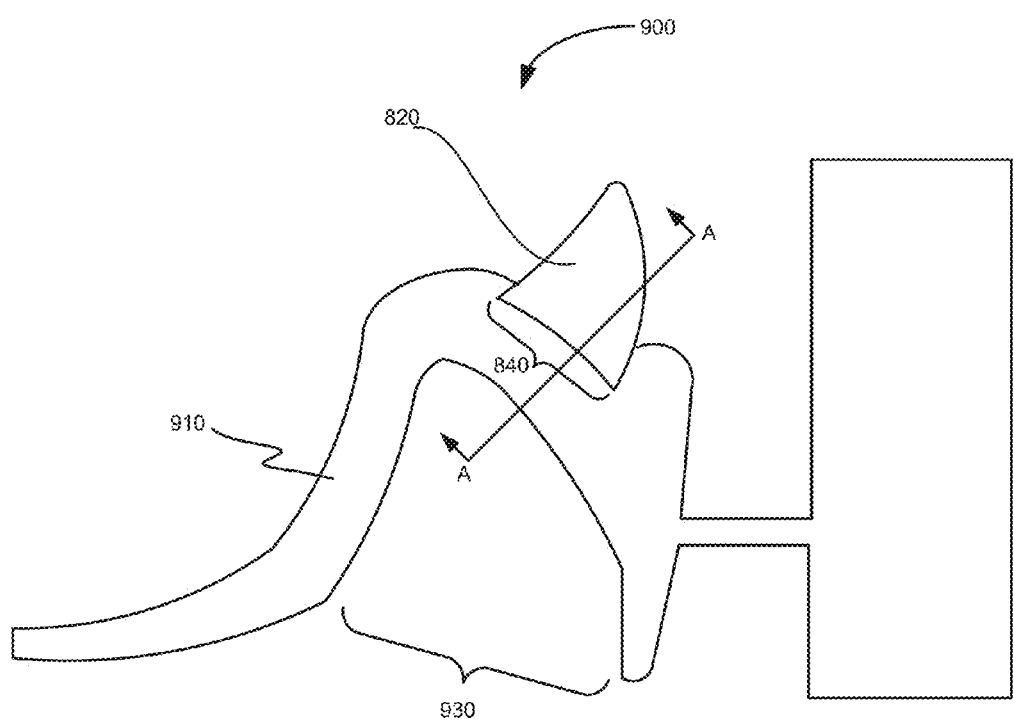
FIG. 9 is a side view of an example embodiment of a layered denture having single layer teeth.
Figure 10:
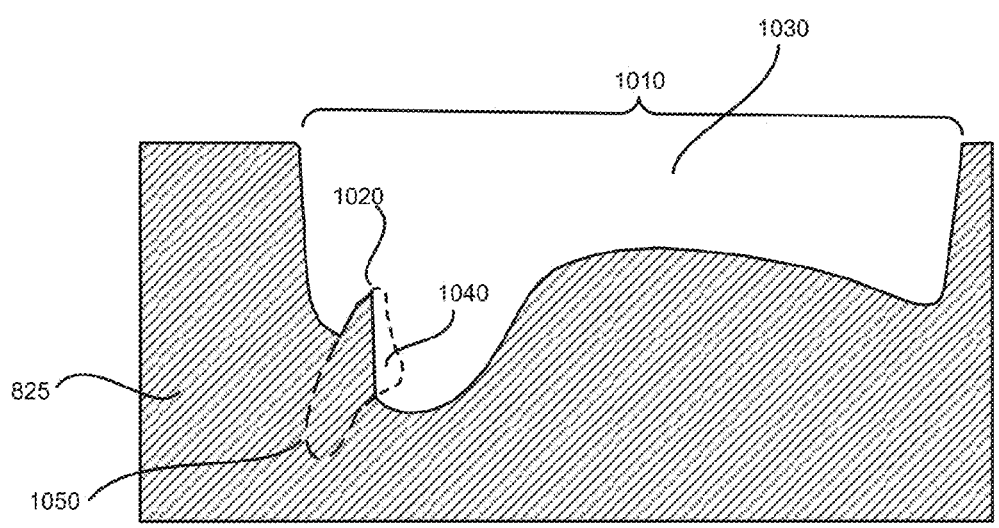
FIGS. 10-12 are side views of an exemplary layered denture having single layer teeth at different points in an exemplary manufacturing process.
Figure 11:
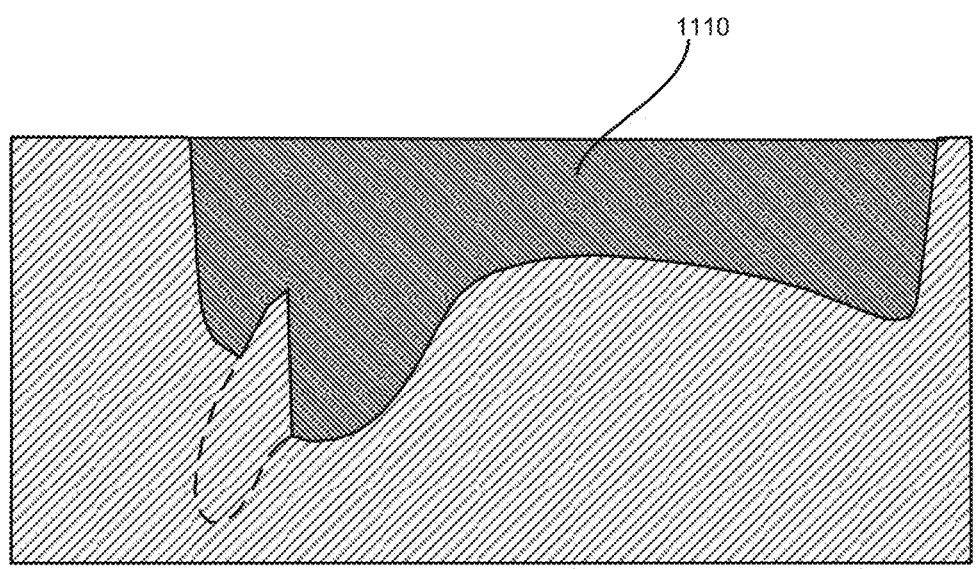
Figure 12:
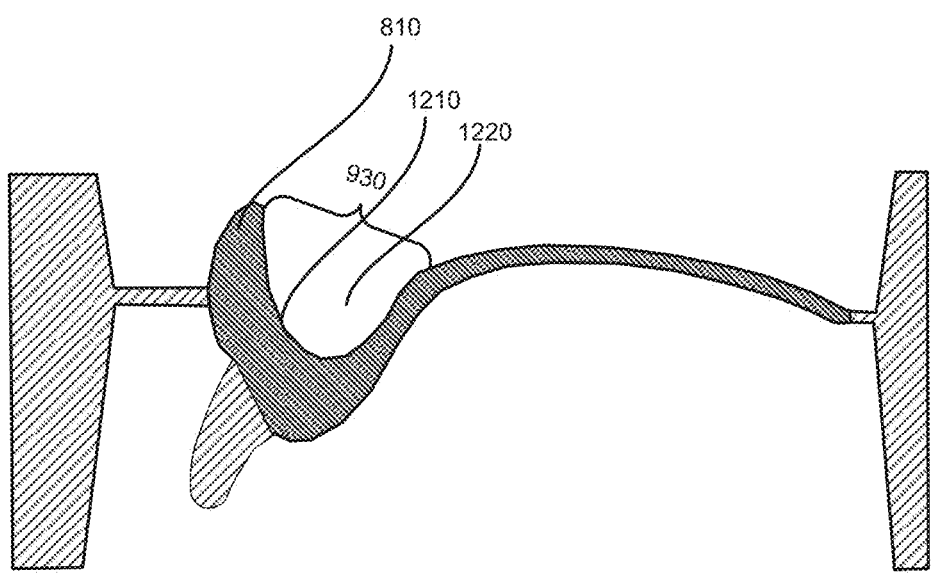

Now, with reference to FIGS. 8 and 9, a section view 800 along line A-A is provided of one example embodiment of a layered denture 900 comprising a base 910 comprising a first material having a first cavity 840; an artificial dentition structure 820 in said first cavity 840 wherein said first cavity 840 is configured to support said artificial dentition structure. An artificial dentition structure 820 may comprise a single layer of material.

In one example embodiment, said base 910 comprises a hardened polymethyl methacrylate (PMMA) material. However, said base may comprise any material having sufficiently low porosity so as to be hygienic for extended placement in a wearer's mouth. For example, said base may be made of a plastic, ceramic, metal, or acrylic, including for instance, a polymer, monomer, composite, or alloy.

Furthermore, said artificial dentition structure 820, said base 910, and any other components of a layered denture 900 may be formed according to a process and system for molding or forming products from thermosetting plastics. Such a system may utilize a deformable container that is placed within the cavity of a housing of a mold with resins and initiator mixed therein. As a piston slides into the cavity, the upper edges of the container may engage between the housing and the piston to seal the housing from leakage. The pressure of the piston along with heat on the housing may enable the curing process to be controlled to maximize compression and minimize porosity. Exemplary processes and systems disclosed in U.S. patent application Ser. No. 13/369,238, PROCESSES AND SYSTEMS FOR MOLDING THERMOSETTING PLASTICS are incorporated by reference.

Furthermore, said base 910 comprising a first material may have a first cavity 840. Said first cavity 840 may be machined by a CAD/CAM machining device, although any process suited for accurate forming of the material maybe utilized. For example, said first pocket may be formed by machining, etching, waterjet, laser cutting, 3D printing, or chemical mask processes.

In one example embodiment, a layered denture 900 may have an artificial dentition structure 820. In one example embodiment, this structure may be at least one tooth. Said tooth may be constructed according to the principles described herein. In various embodiments, the tooth may be constructed of a single layer of material. For example, the artificial dentition structure 820 may comprise high impact acrylic though any material adapted to be wear and abrasion resistant may be used. In some example embodiments, artificial dentition structure 820 may comprise materials processed by exemplary processes and systems disclosed in U.S. patent application Ser. No. 13/369,238, PROCESSES AND SYSTEMS FOR MOLDING THERMOSETTING PLASTICS, which are incorporated by reference. In some example embodiments, these exemplary processes and system enhance the durability of the acrylic or other materials comprising the artificial dentition structure 820. In some example embodiments, said artificial dentition structure 820 is electronically defined to achieve balanced occlusion, in accordance with the principles disclosed herein.

Now, with further reference to FIG. 9, in one embodiment of a layered denture 900, base 910 is machined to conform to the geometry of a wearer's natural dentition. For example, said base 910 comprising a first material may have a base pocket 930. Said base pocket 930 may be machined by a CAD/CAM machining device, although any process suited for accurate forming of the material maybe utilized. For example, said second pocket may be formed by machining, etching, waterjet, laser cutting, 3D printing, or chemical mask processes. As discussed further herein, in various embodiments, base pocket 930 may comprise an edentulous ridge interface surface 1210. Moreover, in various embodiments, base pocket 930 may comprise an implant interface surface. Alternatively, base pocket 930 may comprise any configuration adapted to securely retain the layered denture in a patient's mouth.

Now, with reference to FIGS. 10-12, and FIG. 20, a novel process 2000 of manufacturing a layered denture 900 is provided. Notably, the tooth layer is formed first, followed by the denture base. For example, in various embodiments process 2000 comprises machining a material blank comprising a tooth material wherein the machining forms a first cavity, filling a first denture material with the first cavity wherein the first denture material comprises denture base material, and machining the first denture base material wherein the machining forms an edentulous ridge interface surface. In accordance with various embodiments, each material filled into a cavity may be cured prior to being milled. In various embodiments, said material is cured by exposure to heat and/or pressure. Alternatively, in various embodiments, only the material blank is cured by exposure to heat and/or pressure. In various embodiments, said material is cured by exemplary processes and systems disclosed in U.S. patent application Ser. No. 13/369,238, PROCESSES AND SYSTEMS FOR MOLDING THERMOSETTING PLASTICS, which are incorporated by reference. For instance, the curing process may enhance the strength and resiliency of the material. In this regard, it is often advantageous to form the material blank from the tooth material, thus, permitting the tooth layer to be exposed to the curing process, thus enhancing the strength of the tooth layer more so than the other layers.

With reference to FIGS. 10-12, and FIG. 20 a layered denture may be manufactured by a process 2000 for manufacturing a layered denture 900 comprising machining a material blank 825 comprising tooth material. A first cavity 1010 may be formed in the material blank 825. In various embodiments, the first cavity 1010 comprises a first base boundary 1020 and an aft cavity 1030. In this regard, the first cavity 1010 may approximately outline the shape of a denture base. Moreover, a first base boundary 1020 may be positioned to outline a portion of the shape of an artificial dentition structure illustrated by imaginary line 1050. Moreover, the first base boundary 1020 may be offset to subtract a deleted portion of an artificial dentition structure. For example, deleted portion 1040 of an artificial dentition structure may be deleted via offsetting of first base boundary 1020. In this manner, first cavity 1010 may be shaped with consideration of aesthetic factors, such as the shaping of an artificial dentition structure illustrated by imaginary line 1050, and also structural factors, such as permitting access by machining tools to the area below deleted portion 1040.

In various embodiments, additional material is filled into first cavity 1010 and machined to form a denture base. For example, a first denture material 1110 may be filled into first cavity 1010 and machined to form a denture base 810. In various embodiments, the first denture material 1110 comprises denture base material. In various embodiments, first denture material 1110 is machined to form a denture base. In various embodiments, first denture material 1110 is further machined to form a base pocket 930. In various embodiments, for example, with particular reference to FIG. 12, base pocket 930 may be formed by removing portions of first denture material 1110, and optionally, portions of material blank 825 comprising enamel material. In this regard, base pocket 930 may approximately outline the shape of a denture base. In various embodiments, base pocket 930 forms an edentulous ridge interface surface 1210. In various embodiments, edentulous ridge interface surface 1210 is shaped to conform to a patient's natural mouth structures in order to securely hold the denture in a patient's mouth. Moreover, in various embodiments, base pocket 930 may comprise an implant interface surface. Alternatively, base pocket 930 may comprise any configuration adapted to securely retain the layered denture in a patient's mouth.

Figure 14:
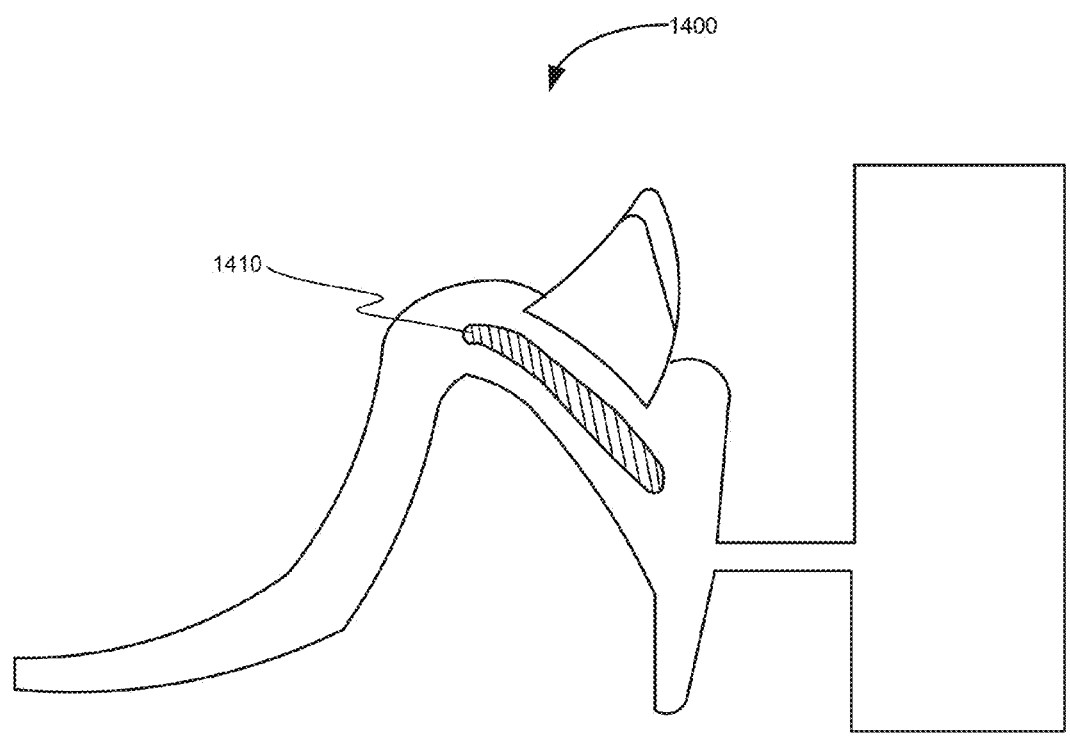
FIG. 14 is a side view of an example embodiment of a layered denture having multi layer teeth and an integrated support layer.

Thus, with reference to FIGS. 2 and 9, it is apparent that in various embodiments, an artificial denture may comprise any number of layers, for example, one layer artificial dentition structures comprising a tooth layer and a one layer denture base, or two layer artificial dentition structures comprising a dentin layer and an enamel layer and a one layer denture base, and/or any configuration having a multilayer base, or a base with a support layer, for example, according to FIG. 14, a layered denture 1400 may additionally comprise a support layer 1410. Other exemplary processes and systems disclosed in U.S. patent application Ser. No. 13/830,963, SYSTEM AND PROCESS FOR MANUFACTURING OF DENTURES, which are incorporated by reference, can also be implemented.

Figure 15:
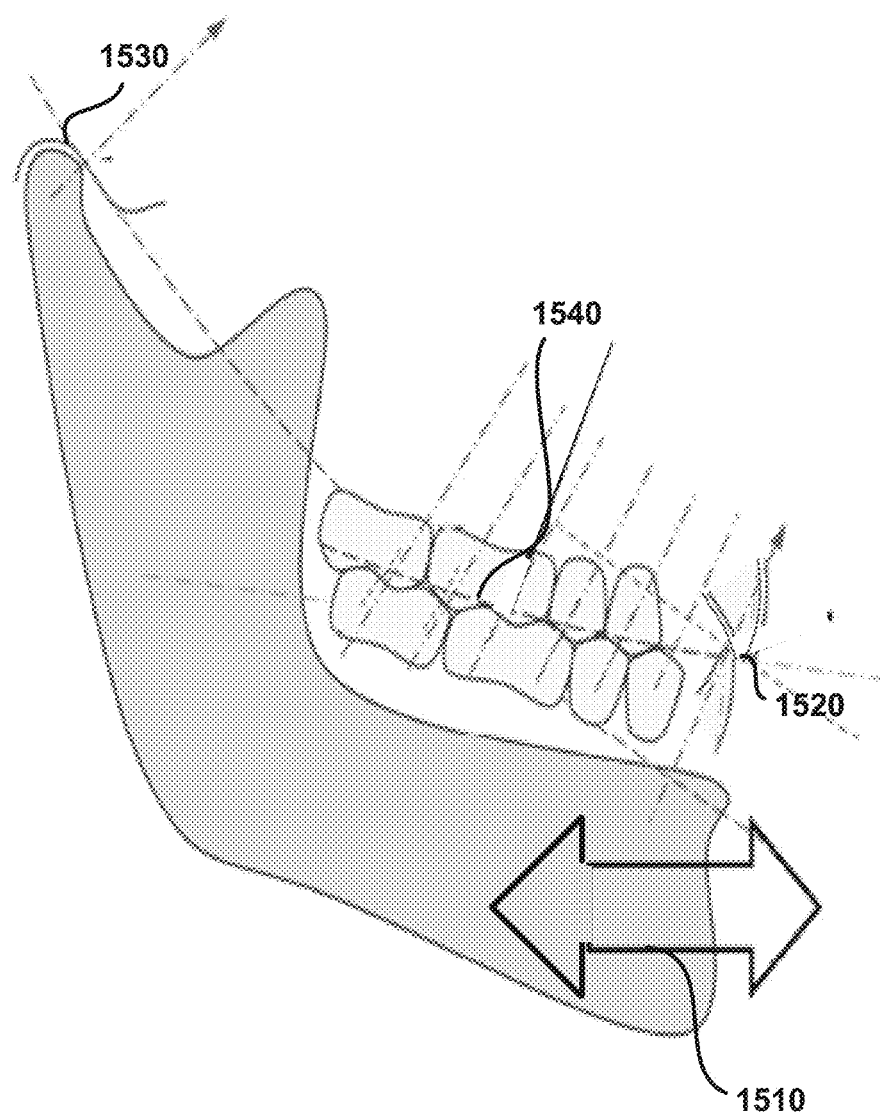
FIGS. 15-16 illustrate an exemplary balanced occlusion motion envelope defined in protrusion and laterotrusion.
Figure 16:
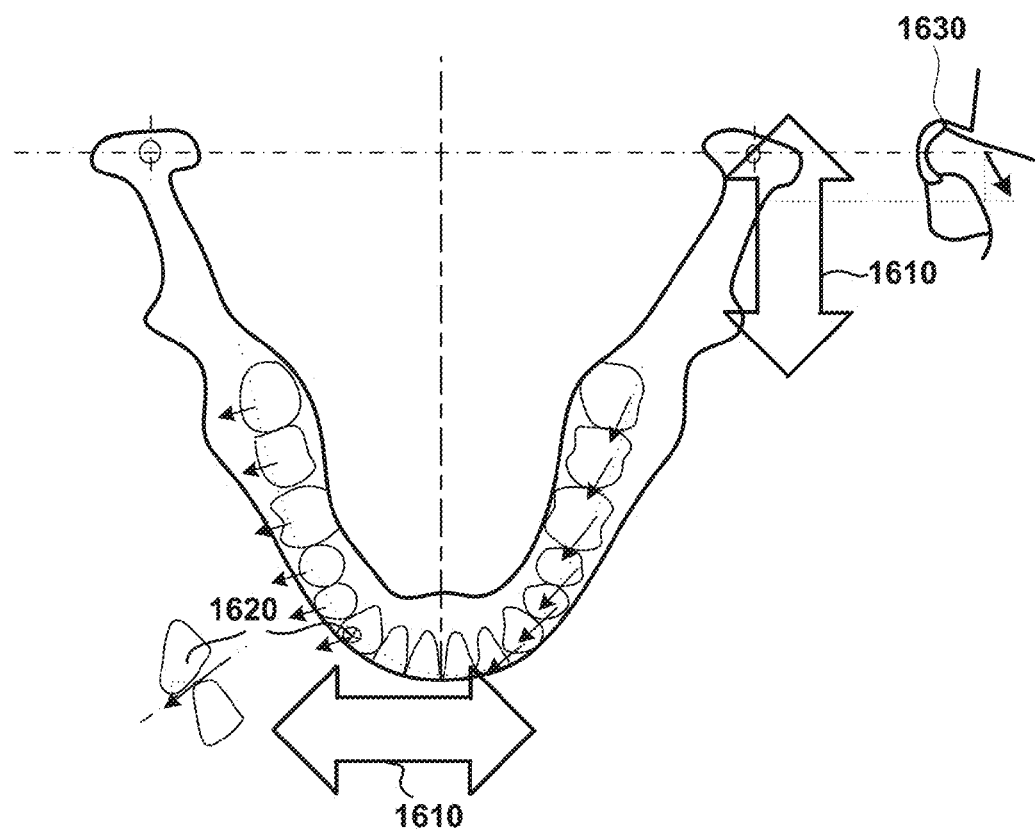

In one example embodiment, machining is in accordance with a three-dimensional file of the patient's anatomy. For example, in one example embodiment, a layered denture may be manufactured with consideration for balanced occlusion of the layered denture when used by a denture user. In one embodiment, artificial dentition structure is electronically defined by computer modeling wherein each layer is designed by defining the motion envelope of the user's mandible and each layer is shaped to accommodate that motion while remaining in contact through much or all of the motion. In one example embodiment, each layer may be defined by prismatic or other geometry. Furthermore, with reference to FIGS. 15 and 16, in one example embodiment, the motion envelope may be defined in protrusion 1510 from centric relation (mandible fully retracted) to protrusion 1510 where the central incisors are edge-to-edge. In one example embodiment, the motion envelope may be defined in laterotrusion 1610 where the buccal cusps of the posterior teeth are vertically aligned. Among other possible constraints, the mandible motion may be constrained in protrusion by incisal guidance 1520 and condylar shape 1530 and in laterotrusion by canine guidance 1620 and condylar shape 1630.

Figure 17:
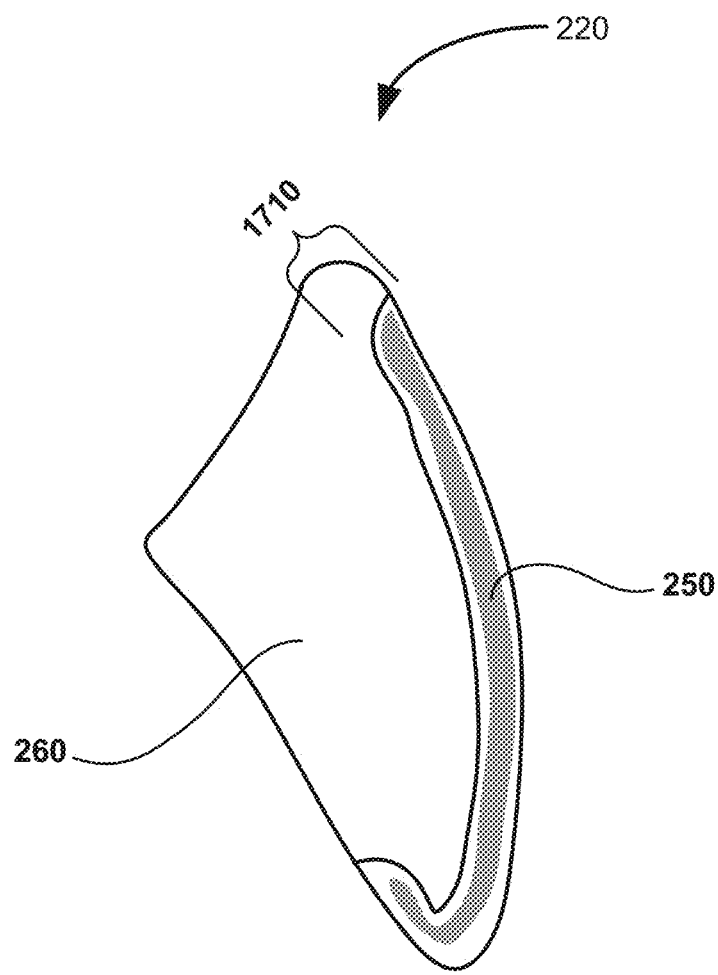
FIG. 17 illustrates a side view of an exemplary artificial dentition structure.
Figure 18:
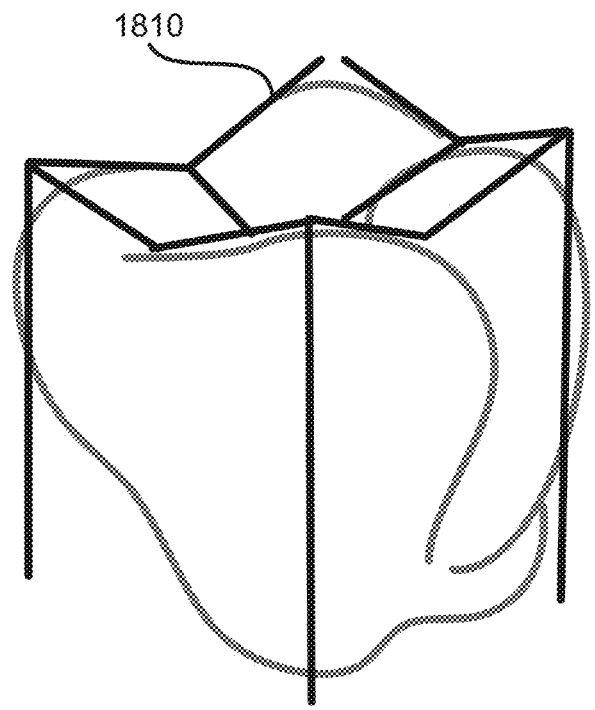
FIG. 18 illustrates exemplary artificial dentition structures.
Figure 18:
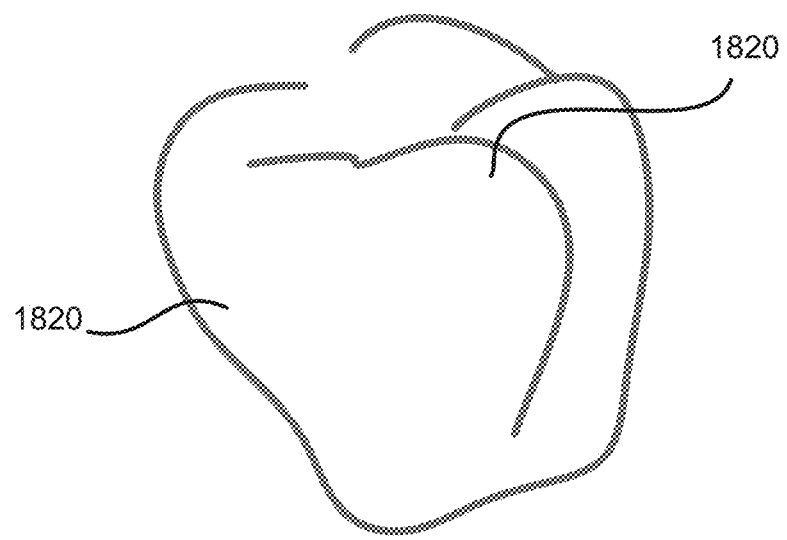
Figure 19:
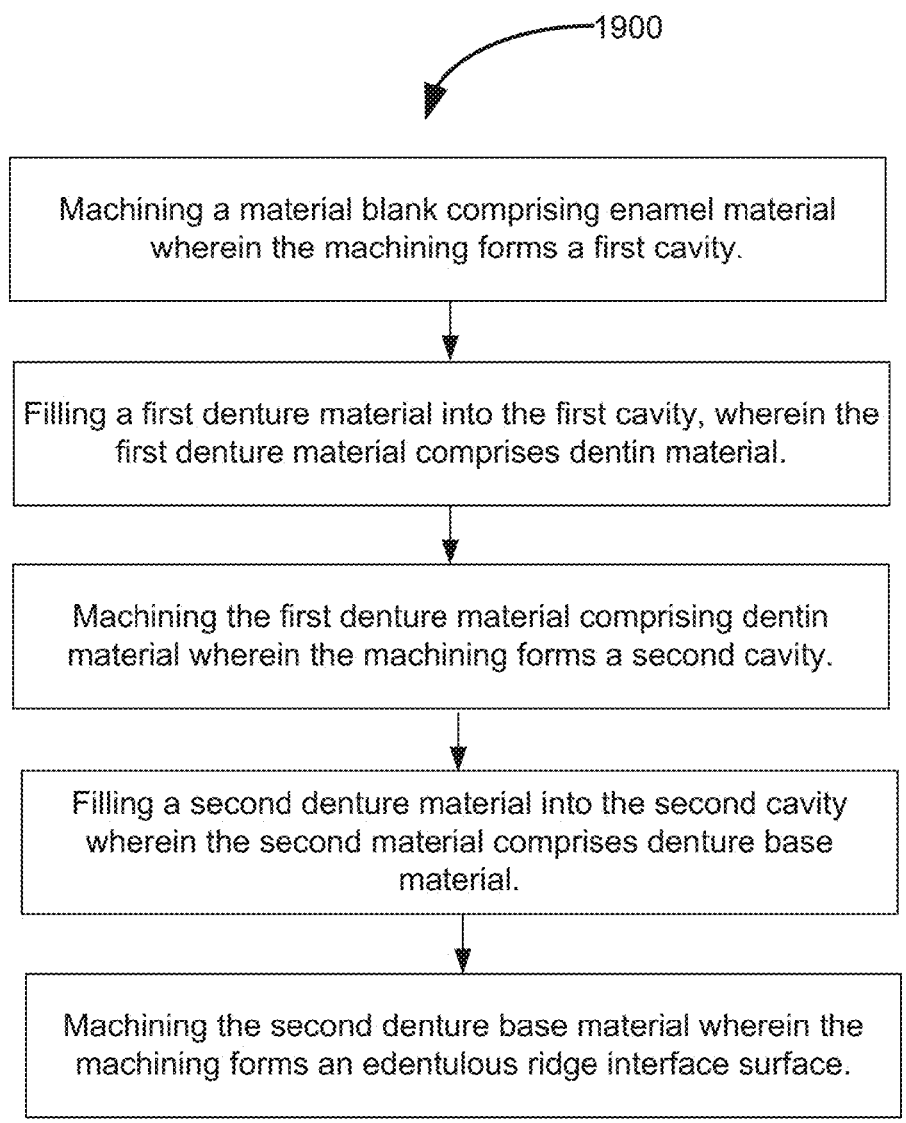
FIGS. 19-20 are flow charts illustrating exemplary methods of manufacturing layered dentures.
Figure 20:
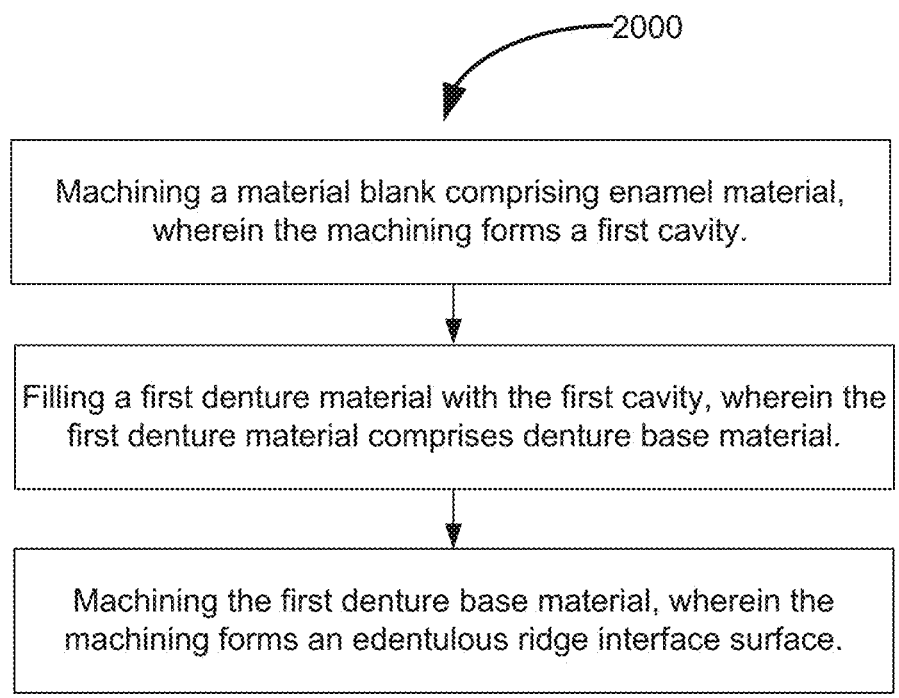

With reference to FIG. 17, in one example embodiment, the shape of artificial dentition structures 220 is defined for the mandible motion envelope and the thickness and shape of dentin layer 260 of an artificial dentition structure 220 is offset (See FIG. 18; 1810) to provide sufficient spacing for balanced occlusion to be achieved upon the formation of enamel layer 250. Thus, both dentin layer 260 and enamel layer 250 of an artificial dentition structure 220 may be electronically defined and may be built based on digital images of the patient's anatomy which takes account of the mandible motion envelope and the offsets to achieve balanced occlusion. In one example embodiment, no grinding on the occlusal surface (See FIG. 15; 1540) of the enamel layer 250 will be required, due, for example, to this offsetting (See FIG. 18, 1810). In one example embodiment, this may result in a more aesthetically pleasing layered denture wherein the denture does not exhibit localized weakening due to grinding away of material. In one example embodiment, additional tooth morphology 1820 may be added, for example, for aesthetic purposes or for any other purpose.

An exemplary manufacturing process may proceed by iterative steps of machining pockets, then filling the machined pockets with a material, then machining the filled material to create a layer. In other exemplary manufacturing processes, multiple steps of machining and filling may occur in parallel, for example, at different locations or surfaces of the layered denture. With reference to FIG. 1, in some example embodiments, at least one of dentin layer 260 and enamel layer 250 may be formed by machining or by 3D printing. In various embodiments, single layer artificial dentition structures comprising a single tooth material may be formed by machining or by 3D printing. In some example embodiments, additional material, for example, bonding material is filled over a layer and machined, for example, with reference to FIG. 14, to embed support layer 1410. However, any manufacturing process causing adhesion or bonding between layers may be utilized. In some embodiments, a layered denture may comprise multiple layers, although any number of layers suitable to form the denture as desired may be implemented.

The process for manufacturing layered dentures may be implemented by an apparatus as describing below. Moreover, it is to be expressly understood that any other systems or apparatus may also implement the process of the present invention.

In one instance, a fixture for holding the layered denture during manufacturing may be located adjacent to a material removing device. In some instances, the material removing device is a CNC or a CAD/CAM mill, although the material removing device can be a mill, grinder, laser cutter, or any other suitable device for forming the structures of the layered denture. In some instances, the material removing device and the fixture are movable relative to one another. In some instances, adjacent to the fixture may be at least one material delivery device to deliver raw material for the filling process described herein. Now, having discussed manufacturing of the reinforcement aspects, a layered denture may be further improved by adding a simulated root structure.

Figure 13:
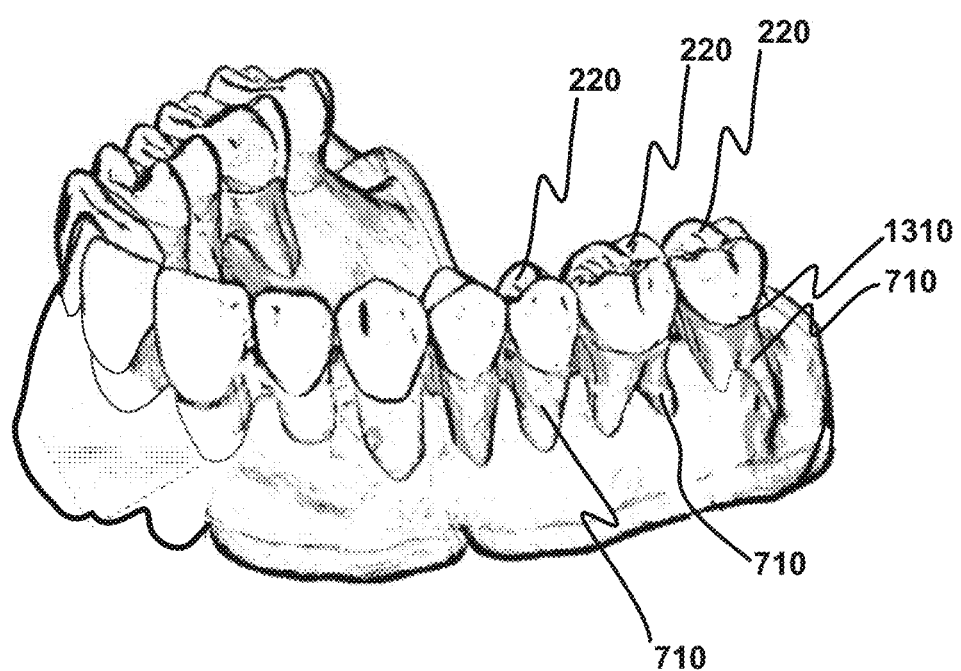
FIG. 13 is a view of an example embodiment of a layered denture having a root approximating structure that simulates anatomical roots.

With reference to FIG. 2 and FIG. 13, in accordance with one example embodiment, and the principles described herein, a layered denture may comprise a base having a first pocket 240 wherein said first pocket 240 is configured to resemble a root of a tooth wherein a simulated root material 710 may be filled into a said first pocket 240. In some example embodiments, said simulated root material 710 provides a surface upon which artificial dentition structure 220 resides. In other example embodiments, said simulated root material is a part of dentin layer 260 of an artificial dentition structure 220. For example, in some example embodiments, said simulated root material 710 may be said earlier described first denture material machined to provide a dentin layer 260. For example, an artificial dentition structure may comprise a first denture material wherein said material is filled into said first pocket 240 and machined to provide at least one of a dentin layer and a root approximating structure.

In some example embodiments, said simulated root material 710 is a different material than said first denture material. For example, an artificial dentition structure may comprise a first denture material wherein said material is filled into said first pocket and machined to provide a root approximating structure; a second tooth dentition material wherein said material is filled into a said first pocket, and machined to provide a dentin layer. Furthermore, an artificial dentition structure may in some example embodiments comprise any number of layers, including for instance, a single layer.

With reference to FIG. 13, a plurality of artificial dentition structures 220 are illustrated in conjunction with simulated root material 710, but with base 210 shaded so as to appear partially transparent. It can be recognized that in this exemplary embodiment, simulated root material 710 extends well below the gum lime 1310.

In addition, it should be noted that exemplary embodiments of a layered denture may include one of a simulated root structure, a support layer and a consideration for balanced occlusion, or any combination of such features. For example, a layered denture may include a support layer with balance occlusion (and without simulated root structure), a support layer with a simulated root structure (without balanced occlusion), a simulated root structure with balanced occlusion (without a support layer, and/or with a convention metal band configuration) or any other arrangement of such features individually or in combination. For purposes of describing the present invention, machining is used to describe the process of removing material from a part. This term, for purposes of the present invention includes but is not limited to milling, 3D printing, grinding, water jetting, laser cutting, electric discharge machining, CNC machining, ultrasonic machining, and any other type of mechanical, chemical, electrical, or other process suitable to conform filled material into to a layer.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "proximate," "proximately," or any other variation thereof, are intended to cover a physical connection, an electrical connection, a magnetic connection, an optical connection, a communicative connection, a functional connection, and/or any other connection. When language similar to "at least one of A, B, or C" is used, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A partially-milled layered denture, the partially-milled denture comprising:
   a tooth material blank having removed portions that form a base cavity;
   a first denture material layer extending into the base cavity, and
      comprising a first base boundary located at a base side of the first denture material, the base boundary defining at least part of the base cavity, wherein the base cavity substantially outlines the shape of a denture base; and
   the tooth material blank further comprising a tooth boundary at a tooth side of the first denture material layer and a tooth portion of the layered tooth material blank at a first tooth boundary, the first tooth boundary separating the first denture material layer from an enamel layer in the layered tooth material blank, a second denture layer added into the base cavity.

2. The partially-milled layered denture according to claim 1, wherein the tooth material blank comprises:
   a puck-shaped solid comprising an annular groove disposed about the outer circumferential edge of the puck shaped solid and proximate to a lower face of the puck-shaped solid.

3. The partially-milled layered denture according to claim 1, wherein the first denture material layer is offset according to a motion envelope to provide sufficient spacing to achieve balanced occlusion.

4. The partially-milled layered denture of claim 1, the first denture layer being partially enclosed by the tooth material blank at the first base boundary.

5. The partially-milled layered denture of claim 1, further comprising a base pocket machined into the second denture material layer.

6. The partially-milled layered denture of claim 5, the base pocket comprising an implant interface surface.

7. The partially-milled layered denture of claim 1, the first denture layer being partially enclosed by the layered tooth material blank at the first base boundary.

8. The partially-milled layered denture of claim 1, wherein the tooth material blank comprises:
   a puck-shaped solid comprising an annular groove disposed about the outer circumferential edge of the puck shaped solid and proximate to a lower face of the puck-shaped solid.

9. The partially-milled layered denture of claim 1, wherein the first denture material layer is offset according to a motion envelope to provide sufficient spacing to achieve balanced occlusion.

10. The partially-milled layered denture of claim 1, the second denture layer comprising a denture base material and a support layer.

11. The partially-milled layered denture according to claim 1, wherein the denture is manufactured further to realize a final denture shape.

12. The partially-milled layered denture of claim 1, wherein the first base boundary is offset to achieve balanced occlusion.

13. The partially-milled layered denture according to claim 1, wherein the denture is manufactured further to realize a final denture shape.

14. The partially-milled layered denture according to claim 1, wherein the denture is shaped according to a patient's anatomy.

15. The partially-milled layered denture according to claim 1, wherein the denture is shaped according to a patient's anatomy.

* * * * *